United States Patent [19]

Desbois et al.

[11] Patent Number: 4,621,160

[45] Date of Patent: Nov. 4, 1986

[54] PROCESS FOR THE CHLORINATION OF AROMATIC DERIVATIVES

[75] Inventors: Michel Desbois, Rillieux; Camille Disdier, Lyons, both of France

[73] Assignee: Rhone-Poulenc Specialites Chimiques, Courbevoie, France

[21] Appl. No.: 623,466

[22] Filed: Jun. 22, 1984

[30] Foreign Application Priority Data

Jun. 23, 1983 [FR] France .................................. 83 10373

[51] Int. Cl.$^4$ .............................................. C07C 17/12
[52] U.S. Cl. .................................... 570/207; 570/208; 568/74; 568/649; 568/656
[58] Field of Search .................. 570/207, 208; 568/74, 568/649, 656

[56] References Cited

U.S. PATENT DOCUMENTS 2,881,224 4/1959 McCaulay ........................... 570/208

Primary Examiner—Charles F. Warren
Assistant Examiner—John A. Sopp
Attorney, Agent, or Firm—Finnegan, Henderson, Farabow, Garrett & Dunner

[57] ABSTRACT

A process for the chlorination of aromatic derivatives. The aromatic derivative is reacted with chlorine gas in liquid hydrofluoric acid. The products obtained are useful as intermediates for the synthesis of compounds having a plant-protecting or pharmaceutical activity.

11 Claims, No Drawings

PROCESS FOR THE CHLORINATION OF AROMATIC DERIVATIVES

The present invention relates to a process for the chlorination of aromatic derivatives.

It relates more particularly to a process for the chlorination of aromatic derivatives by reaction with chlorine gas.

It has been known for a long time to attach chlorine to an aromatic nucleus at low temperature by a catalytic method using ferric chloride. One of the major disadvantages of this process is that the catalyst cannot be recycled and, furthermore its removal presents significant problems of harmful effects and pollution. In view of the current efforts to protect the environment, and the plans for antipollution standards, attempts have been made for a long time to find a chlorination process avoiding the use of ferric chloride, the harmful environmental effects of which are known to those skilled in the art.

Another disadvantage of the use of $FeCl_3$ as a catalyst is the fact that this product is extremely difficult to separate off or to destroy at the end of the reaction.

Moreover, in the very particular case of the chlorination of aromatic trifluoromethyl compounds using ferric chloride, defluorination phenomena appear which reduce the yield. Attempts have therefore been made to dispense with this catalyst based on $FeCl_3$.

Thus, German Pat. No. 1,034,609 is known in the prior art; this describes a process for the chlorination of aromatic derivatives using a catalyst consisting of platinum and a metal halide such as, for example, $PdCl_3$, fixed to a support consisting of alumina.

Also, German Pat. No. 825,397 describes a process making it possible to chlorinate aromatic derivatives using a catalyst consisting of boron trifluoride.

U.S. Pat. No. 2,881,224 is also known; this describes the chlorination of aromatic derivatives in the presence of $BF_3$ is hydrofluoric acid.

In contrast to a long-established technical presumption leading those skilled in the art to consider that the chlorination of aromatic derivatives could only be carried out by a catalytic method, it has been discovered that it is possible to carry out this chlorination without a catalyst.

In fact, the present invention relates to a process for the chlorination of aromatic derivatives, which comprises reacting the aromatic derivative with chlorine gas in liquid hydrofluoric acid.

The present process can be used to chlorinate any aromatic derivatives, irrespective of the substituents present on the nucleus. It is possible to use, in particular, benzene derivatives and polycyclic derivatives such as those of naphthalene and anthracene.

The position of attachment of the chlorine to the nucleus will be according to the substitution rules well known to those skilled in the art, as a function of the presence of other ortho-, para- or meta-directing radicals.

The hydrofluoric acid used for the present invention is preferably anhydrous. The molar ratio of the hydrofluoric acid to the starting aromatic compound is preferably between 5 and 50. Values outside this limit are not excluded from the scope of the invention.

The quantity of chlorine used is fixed by those skilled in the art, taking into account whether the desired product corresponds to monochlorination or polychlorination. For monochlorination, the reaction is preferably carried out in the presence of a stoichiometric deficit of chlorine, that is to say with a molar ratio of chlorine to aromatic compound preferably of between 0.5 and 0.9. For polychlorination, the reaction is preferably carried out with an excess of chlorine. The chlorine can be employed in a sealed enclosure under autogenous pressure (generally 1 to 50 bar) or under atmospheric pressure, by bubbling, or in any other device known to those skilled in the art.

The temperature at which the reaction is carried out is preferably between $-20°$ C. and $150°$ C.

If the temperature is to be above $20°$ C., the reaction will have to take place under pressure because the hydrofluoric acid must be liquid.

The reaction time varies from a few minutes to a few hours.

This reaction time varies with the number of chlorine atoms which it is desired to attach to the nucleus, and also with the starting materials and the reaction temperature.

The final chlorinated aromatic product is isolated, for example by distillation of the hydrofluoric acid, which can thus be recovered and recycled, this being an important advantage of the process of the invention.

It can also be isolated by extraction with organic solvents well known to those skilled in the art.

Although the invention is not limited to these compounds it has a particularly advantageous application in the chlorination of perfluoroalkyl, perfluoroalkoxy and perfluorothioalkyl aromatic derivatives such as, for example, trifluoromethyl ($-CF_3$), trifluoromethoxy ($-OCF_3$) and trifluorothiomethyl ($-SCF_3$) aromatic derivatives. These chlorinated derivatives are used in the pharmaceutical and plant protection industries.

Examples which may be mentioned of products which can be used in the process of the present invention are: trifluoromethylbenzene, benzoyl chloride, phenol, nitrobenzene, p-chlorotrifluoromethylbenzene, p-fluoronitrobenzene, 2,4-dichlorophenol, o-nitrotoluene, chlorobenzene, fluorobenzene, benzoic acid, m-bistrifluoromethylbenzene, aniline, acetophenone benzophenone, anisole, toluene, anthracene, diphenyl ether, o-cresol, salicylic acid, trifluoromethoxybenzene and trifluoromethylthiobenzene.

The present invention will be understood more easily with the aid of the examples which follow, which are given by way of indication but without implying a limitation.

EXAMPLE 1

100 ml (5 mol) of anhydrous hydrofluoric acid and 7.8 g (0.1 mol) of benzene are introduced into a 250 ml reactor equipped with a magnetic stirrer bar and cooled to about $0°$ C. The reactor is closed and brought to a pressure of 4 bar (at $0°$ C.) with chlorine gas.

The whole is then heated at $27°$ C. for 3 hours 45 minutes, with stirring. After cooling to about $0°$ C. again, the reactor is decompressed and the crude reaction mixture obtained is introduced onto 110 g of crushed ice. The heterogeneous mixture resulting from this treatment is extracted 3 times with 100 $cm^3$ of methylene chloride. After decantations, the organic phases are combined, washed 2 times with 100 $cm^3$ of softened water and dried. Analyses carried out by gas chromatography (% area), IR spectrometry and mass spectrometry give the following result:

| | |
|---|---|
| benzene | 10.3% |
| monochlorobenzene | 77.6% |
| p-dichlorobenzene | 7.6% |
| o-dichlorobenzene | 4.5% |

EXAMPLE 2

The procedure is identical to that of Example 1, the compounds and conditions being those given below and the treatment of the crude reaction mixture with ice being replaced with extraction of this crude mixture 2 times using 100 cm$^3$ of carbon tetrachloride, these organic phases subsequently being treated in the normal way.

| | |
|---|---|
| Anhydrous hydrofluoric acid | 100 g (5 mol) |
| Trifluoromethylbenzene | 29.2 g (0.2 mol) |
| Temperature | 80° C. |
| Chlorine pressure | 5 bar at 20° C. |
| Duration | 4 hours |

Analyses carried out by gas chromatography (% area), IR spectrometry and mass spectrometry give the following result:

| | |
|---|---|
| trifluoromethylbenzene | 59% |
| o-chlorotrifluoromethylbenzene | 2% |
| m-chlorotrifluoromethylbenzene | 28% |
| p-chlorotrifluoromethylbenzene | 5% |
| polychlorotrifluoromethylbenzenes | 6% |

EXAMPLE 3

The procedure is identical to that of Example 1, the compounds and conditions being as follows:

| | |
|---|---|
| Anhydrous hydrofluoric acid | 50 g (2.5 mol) |
| Benzoyl chloride | 14.1 g (0.1 mol) |
| Temperature | 80° C. |
| Chlorine pressure | 6 bar at 20° C. |
| Duration | 4 hours |

Analyses carried out by gas chromatography (% area), IR spectrometry and mass spectrometry give the following result:

| | |
|---|---|
| benzoyl fluoride | 78.3% |
| m-chlorobenzoyl fluoride | 16.8% |
| o-, p- and poly-chlorobenzoyl fluorides | 4.9% |

EXAMPLE 4.

The procedure is identical to that of Example 1, the compounds and conditions being those given below and the treatment of the crude reaction mixture with ice being replaced by distillation of this crude mixture up to a bottom temperature of 80° C., under atmospheric pressure, in order to remove as much of the hydrofluoric acid solvent as possible:

| | |
|---|---|
| Anhydrous hydrofluoric acid | 60 g (3 mol) |
| Phenol | 9.5 g (0.1 mol) |
| Temperature | about −20° C. |
| Chlorine pressure | 4 bar at −30° C. |
| Duration | 3 hours 15 minutes |

Analyses carried out by gas chromatography (% area), IR spectrometry and mass spectrometry give the following result:

| | |
|---|---|
| phenol | 48.7% |
| p-chlorophenol | 37% |
| o-chlorophenol | 7% |
| polychlorophenols | 17.3% |

EXAMPLE 5

The procedure is identical to that of Example 1, the compounds and conditions being as follows:

| | |
|---|---|
| Anhydrous hydrofluoric acid | 50 g (2.5 mol) |
| Nitrobenzene | 12.3 g (0.1 mol) |
| Temperature | 100° C. |
| Chlorine pressure | 5 bar at 20° C. |
| Duration | 23 hours |

Analyses carried out by gas chromatography (% area), IR spectrometry and mass spectrometry give the following result:

| | |
|---|---|
| nitrobenzene | 61.5% |
| m-chloronitrobenzene | 26.6% |
| other chloronitrobenzenes | 11.9% |

EXAMPLE 6

The procedure is identical to that of Example 1, the compounds and conditions being as follows:

| | |
|---|---|
| Anhydrous hydrofluoric acid | 100 g (5 mol) |
| p-Chlorotrifluoromethylbenzene | 18 g (0.1 mol) |
| Temperature | 80° C. |
| Chlorine pressure | 5 bar at 20° C. |
| Duration | 22 hours 20 min. |

Analyses carried out by gas chromatography (% area), IR spectrometry and mass spectrometry give the following result:

| | |
|---|---|
| p-chlorotrifluoromethylbenzene | 28% |
| 3,4-dichlorotrifluoromethylbenzene | 69% |
| other chlorotrifluoromethylbenzenes | 3% |

EXAMPLE 7

The procedure is identical to that of Example 1, the compounds and conditions being as follows:

| | |
|---|---|
| Anhydrous hydrofluoric acid | 100 g (5 mol) |
| p-Fluoronitrobenzene | 14.1 g (0.1 mol) |
| Temperature | 100° C. |
| Chlorine pressure | 5 bar at 20° C. |
| Duration | 5 hours 40 minutes |

Analyses carried out by gas chromatography (% area), IR spectrometry and mass spectrometry give the following result:

| p-fluoronitrobenzene | 97.1% |
|---|---|
| 4-fluoro-3-chloronitrobenzene | 2.9% |

EXAMPLE 8

The procedure is identical to that of Example 1, the compounds and conditions being as follows:

| Anhydrous hydrofluoric acid | 100 g (5 mol) |
|---|---|
| 2,4-Dichlorophenol | 16.3 g (0.1 mol) |
| Temperature | 100° C. |
| Chlorine pressure | 6 bar at 20° C. |
| Duration | 18 hours 45 min. |

Analyses carried out by gas chromatography (% area), IR spectrometry and mass spectrometry give the following result:

| 2,4-dichlorophenol | 22% |
|---|---|
| trichlorophenol | 73% |
| tetrachlorophenol | 1% |

EXAMPLE 9

The procedure is identical to that of Example 1, the compounds and conditions being as follows:

| Anhydrous hydrofluoric acid | 100 g (5 mol) |
|---|---|
| o-Nitrotoluene | 27.4 g (0.2 mol) |
| Temperature | 20° C. |
| Chlorine pressure | 5 bar at 20° C. |
| Duration | 4 hours |

Analyses carried out by gas chromatography (% area) and mass spectrometry give the following result:

| o-nitrotoluene | 96% |
|---|---|
| chloro-o-nitrotoluene | 4% |

EXAMPLE 10

The procedure is identical to that of Example 1, the compounds and conditions being as follows:

| Anhydrous hydrofluoric acid | 100 g (5 mol) |
|---|---|
| Chlorobenzene | 22.5 g (0.2 mol) |
| Temperature | 20° C. |
| Chlorine pressure | 5 bar at 20° C. |
| Duration | 4 hours |

Analyses carried out by gas chromatography (% area), IR spectrometry and mass spectrometry give the following result:

| chlorobenzene | 82% |
|---|---|
| p-dichlorobenzene | 13% |
| o-dichlorobenzene | 5% |

EXAMPLE 11

The procedure is identical to that of Example 1, the compounds and conditions being as follows:

| Anhydrous hydrofluoric acid | 100 g (5 mol) |
|---|---|
| Fluorobenzene | 9.6 g (0.1 mol) |
| Temperature | 20° C. |
| Chlorine pressure | 5 bar at 20° C. |
| Duration | 20 hours |

Analyses carried out by gas chromatography (% area), IR spectrometry and mass spectrometry give the following result:

| fluorobenzene | 0% |
|---|---|
| p-chlorofluorobenzene | 76.5% |
| o-chlorofluorobenzene | 1.3% |
| dichlorofluorobenzenes | 21.4% |
| trichlorofluorobenzenes | 0.8% |

EXAMPLE 12

The procedure is identical to that of Example 1, the compounds and conditions being as follows:

| Anhydrous hydrofluoric acid | 100 g (5 mol) |
|---|---|
| Benzoic acid | 12.2 g (0.1 mol) |
| Temperature | 100° C. |
| Chlorine pressure | 5 bar at 20° C. |
| Duration | 23 hours 45 min. |

Analyses carried out by gas chromatography (% area), IR spectrometry and mass spectrometry give the following result:

| benzoic acid | 29% |
|---|---|
| m-chlorobenzoic acid | 71% |

EXAMPLE 13

The procedure is identical to that of Example 1, the compounds and conditions being as follows:

| Anhydrous hydrofluoric acid | 100 g (5 mol) |
|---|---|
| m-Bistrifluoromethylbenzene | 21.4 g (0.1 mol) |
| Temperature | 80° C. |
| Chlorine pressure | 5 bar at 20° C. |
| Duration | 18 hours |

Analyses carried out by gas chromatography (% area), IR spectrometry and mass spectrometry give the following result:

| m-bistrifluoromethylbenzene | 97.7% |
|---|---|
| chloro-m-bistrifluoromethylbenzene | 2.3% |

EXAMPLE 14

The procedure is identical to that of Example 1, the compounds and conditions being as follows:

| Anhydrous hydrofluoric acid | 100 g (5 mol) |
|---|---|
| Aniline | 9.3 g (0.1 mol) |
| Temperature | 120° C. |
| Chlorine pressure | 5 bar at 20° C. |
| Duration | 18 hours |

Analyses carried out by gas chromatography (% area), IR spectrometry and mass spectrometry give the following result:

| | |
|---|---|
| aniline | 78% |
| m- and/or p-chloroaniline | 6% |
| o-chloroaniline | 0.8% |
| polychloroaniline | 15.2% |

EXAMPLE 15

The procedure is identical to that of Example 1, the compounds and conditions being as follows:

| | |
|---|---|
| Anhydrous hydrofluoric acid | 100 g (5 mol) |
| Acetophenone | 12 g (0.1 mol) |
| Temperature | 80° C. |
| Chlorine pressure | 4 bar at 20° C. |
| Duration | 18 hours |

Analyses carried out by gas chromatography (% area), IR spectrometry and mass spectrometry give the following result:

| | |
|---|---|
| acetophenone | 60% |
| di- and tri-chloromethyl phenyl ketone | 30.1% |
| chloroacetophenones | 7% |

EXAMPLE 16

The procedure is identical to that of Example 1, the compounds and conditions being as follows:

| | |
|---|---|
| Anhydrous hydrofluoric acid | 100 g (5 mol) |
| Benzophenone | 18.2 g (0.1 mol) |
| Temperature | 80° C. |
| Chlorine pressure | 4 bar at 20° C. |
| Duration | 27 hours |

Analyses carried out by gas chromatography (% area), IR spectrometry and mass spectrometry give the following result:

| | |
|---|---|
| benzophenone | 43% |
| monochlorobenzophenones | 20% |
| polychlorobenzophenones | 37% |

EXAMPLE 17

The procedure is identical to that of Example 1, the compounds and conditions being as follows:

| | |
|---|---|
| Anhydrous hydrofluoric acid | 100 g (5 mol) |
| Aniline | 9.3 g (0.1 mol) |
| Temperature | 25° C. |
| Chlorine pressure | 4 bar at 0° C. |
| Duration | 19 hours |

Analyses carried out by gas chromatography (% area), IR spectrometry and mass spectrometry give the following result:

| | |
|---|---|
| aniline | 96% |
| p- and/or m-chloroaniline | 2% |
| o-chloroaniline | 1% |
| dichloroaniline | 1% |

EXAMPLE 18

The procedure is identical to that of Example 1, the compounds and conditions being as follows:

| | |
|---|---|
| Anhydrous hydrofluoric acid | 100 g (5 mol) |
| Anisole | 10.8 g (0.1 mol) |
| Temperature | 20° C. |
| Chlorine pressure | 4 bar at 20° C. |
| Duration | 2 hours 30 minutes |

Analyses carried out by gas chromatography (% area), IR spectrometry and mass spectrometry give the following result:

| | |
|---|---|
| anisole | 5% |
| p-chloroanisole | 43% |
| o-chloroanisole | 25.5% |
| polychloroanisoles | 26.5% |

EXAMPLE 19

The procedure is identical to that of Example 1, the compounds and conditions being as follows:

| | |
|---|---|
| Hydrofluoric acid | 50 g (2.5 mol) |
| Toluene | 9.2 g (0.1 mol) |
| Temperature | 10° C. |
| Chlorine pressure | 4 bar at 10° C. |
| Duration | 4 hours 15 min. |

Analyses carried out by gas chromatography (% area), IR spectrometry and mass spectrometry give the following result:

| | |
|---|---|
| toluene | 14% |
| monochlorotoluene | 71% |
| polychlorotoluene | 15% |

EXAMPLE 20

The procedure is identical to that of Example 1, the compounds and conditions being as follows:

| | |
|---|---|
| Anhydrous hydrofluoric acid | 100 g (5 mol) |
| Anthracene | 12.8 g (0.1 mol) |
| Temperature | 20° C. |
| Chlorine pressure | 4 bar at 20° C. |
| Duration | 4 hours 30 minutes |

Analyses carried out by gas chromatography (% area), IR spectrometry and mass spectrometry give the following result:

| | |
|---|---|
| anthracene | 61% |
| monochloroanthracenes | 12% |
| polychloroanthracenes | 27% |

EXAMPLE 21

The procedure is identical to that of Example 1, the compounds and conditions being as follows:

| Anhydrous hydrofluoric acid | 20 g (1 mol) |
|---|---|
| Diphenyl ether | 17 g (0.1 mol) |
| Temperature | 20° C. |
| Chlorine pressure | 2 bar at 20° C. |
| Duration | 19 hours 30 min. |

Analyses carried out by gas chromatography (% area), IR spectrometry and mass spectrometry give the following result:

| diphenyl ether | 62% |
|---|---|
| monochlorodiphenyl ether | 25.3% |
| polychlorodiphenyl ether | 12.7% |

EXAMPLE 22

The procedure is identical to that of Example 1, the compounds and conditions being as follows:

| Anhydrous hydrofluoric acid | 50 g (2.5 mol) |
|---|---|
| o-Cresol | 10.8 g (0.1 mol) |
| Temperature | 10° C. |
| Chlorine pressure | 4 bar at 10° C. |
| Duration | 19 hours 15 min. |

Analyses carried out by gas chromatography (% area), IR spectrometry and mass spectrometry give the following result:

| o-cresol | 66.7% |
|---|---|
| 4-chloro-2-methylphenol | 18.2% |
| other chloro-o-cresols | 15.1% |

EXAMPLE 23

The procedure is identical to that of Example 1, the compounds and conditions being as follows:

| Anhydrous hydrofluoric acid | 100 g (5 mol) |
|---|---|
| Salicylic acid | 13.8 g (0.1 mol) |
| Temperature | 80° C. |
| Chlorine pressure | 5 bar at 20° C. |
| Duration | 23 hours 20 min. |

Analyses carried out by gas chromatography (% area), IR spectrometry and mass spectrometry give the following result:

| salicylic acid | 0% |
|---|---|
| 5-chloro-2-hydroxybenzoic acid | 68.5% |
| 3-chloro-2-hydroxybenzoic acid | 10% |
| 3,5-dichloro-2-hydroxybenzoic acid | 20.5% |

EXAMPLE 24

The procedure is identical to that of Example 1, the compounds and conditions being as follows:

| Anhydrous hydrofluoric acid | 50 g (2.5 mol) |
|---|---|
| Trifluoromethoxybenzene | 16.2 g (0.1 mol) |
| Temperature | 50° C. |
| Chlorine pressure | 4 bar at 20° C. |
| Duration | 5 hours 15 minutes |

Analyses carried out by gas chromatography (% area), IR spectrometry and mass spectrometry give the following result:

| trifluoromethoxybenzene | 24% |
|---|---|
| p-chlorotrifluoromethoxybenzene | 64.5% |
| o-chlorotrifluoromethoxybenzene | 10% |
| dichlorotrifluoromethoxybenzene | 1.5% |

EXAMPLE 25

The procedure is identical to that of Example 1, the compounds and conditions being as follows:

| Anhydrous hydrofluoric acid | 25 g (1.25 mol) |
|---|---|
| Trifluoromethylthiobenzene | 4.45 g (0.025 mol) |
| Temperature | 50° C. |
| Chlorine pressure | 4 bar at 20° C. |
| Duration | 5 hours 15 min. |

Analyses carried out by gas chromatography (% area), IR spectrometry and mass spectrometry give the following result:

| trifluoromethylthiobenzene | 0% |
|---|---|
| monochlorotrifluoromethylthiobenzene | 0.5% |
| dichlorotrifluoromethylthiobenzene | 4.2% |
| trichlorotrifluoromethylthiobenzene | 74% |
| other chlorotrifluoromethylthiobenzenes | 21.3% |

EXAMPLE 26

The procedure is identical to that of Example 1, but the reaction is carried out at atmospheric pressure and the chlorine is introduced by being bubbled into the reaction medium, the compounds and conditions being as follows:

| Anhydrous hydrofluoric acid | 100 g (5 mol) |
|---|---|
| Benzyl alcohol | 10.8 g (0.1 mol) |
| Temperature | 0° C. |
| Chlorine pressure | atmospheric p. |
| Duration | 1 hour 10 minutes |

Analyses carried out by IR spectrometry give the following result:

Presence of a polymer chlorinated on the aromatic nucleus, having the structure:

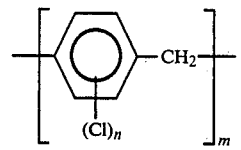

EXAMPLE 27

The procedure is identical to that of Example 1, the compounds and conditions being as follows:

| | |
|---|---|
| Anhydrous hydrofluoric acid | 50 g (2.5 mol) |
| 2-chloro-4-trifluoromethylphenol | 9.8 g (0.05 mol) |
| Temperature | 48° C. |
| Chlorine pressure | 4 bar at 20° C. |
| Duration | 4 hours |

Analyses carried out by gas chromatography (% area), IR spectrometry and mass spectrometry give the following result:

| | |
|---|---|
| 2,6-dichloro-4-trifluoromethylphenol and 2,5-dichloro-4-trifluoromethylphenol | 88% |
| trichloro-4-trifluoromethylphenol | 8% |

What is claimed is:

1. A process for the chlorination of an aromatic derivative comprising the step of reacting the aromatic derivative with chlorine gas in liquid hydrofluoric acid for a time sufficient to effect chlorination of the aromatic ring of said aromatic derivative, wherein said reaction is carried out in the absence of a catalyst.

2. The process of claim 1, wherein the hydrofluoric acid is anhydrous.

3. The process of claim 2, wherein the molar ratio of hydrofluoric acid to aromatic derivative ranges from 5 to 50.

4. The process of claim 1, wherein the molar ratio of hydrofluoric acid to aromatic derivative ranges from 5 to 50.

5. The process of claim 4, wherein said molar ratio ranges from 25 to 50.

6. The process of claim 1, wherein the chlorination is carried out from −20° C. to 150° C.

7. The process of claim 6, wherein said chlorination is carried out from −20° to 120° C.

8. The process of claim 1, wherein the chlorination is carried out under autogenous pressure.

9. The process of claim 1, wherein the chlorination is carried out under atmospheric pressure.

10. The process of claim 1, wherein the aromatic derivative is selected from the group consisting of perfluoroalkyl, perfluoroalkoxy and perfluorothioalkyl aromatic derivatives.

11. The process of claim 10, wherein the aromatic derivative is selected from the group consisting of trifluoromethylbenzenes, trifluoromethoxybenzenes and trifluoromethylthiobenzenes.

* * * * *